United States Patent
Buchbinder et al.

(10) Patent No.: US 10,208,259 B2
(45) Date of Patent: Feb. 19, 2019

(54) ALIPHATIC CRACKING AND DEALKYLATION WITH HYDROGEN DILUENT

(71) Applicant: UOP LLC, Des Plaines, IL (US)

(72) Inventors: Avram M. Buchbinder, Skokie, IL (US); Stanley J. Frey, Palatine, IL (US); Hayim Abrevaya, Kenilworth, IL (US); Falaah Falih, Mount Prospect, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 15/783,777

(22) Filed: Oct. 13, 2017

(65) Prior Publication Data

US 2018/0179453 A1    Jun. 28, 2018

Related U.S. Application Data

(60) Provisional application No. 62/439,337, filed on Dec. 27, 2016.

(51) Int. Cl.
| | | |
|---|---|---|
| C07C 4/06 | (2006.01) | |
| C10G 47/04 | (2006.01) | |
| B01J 29/40 | (2006.01) | |
| C07C 4/18 | (2006.01) | |
| C07C 15/40 | (2006.01) | |
| B01D 3/14 | (2006.01) | |
| C10G 47/24 | (2006.01) | |

(52) U.S. Cl.
CPC .............. *C10G 47/04* (2013.01); *B01J 29/40* (2013.01); *C07C 4/06* (2013.01); *C07C 4/18* (2013.01); *C07C 15/40* (2013.01); *B01D 3/14* (2013.01); *C07C 2529/06* (2013.01); *C07C 2529/40* (2013.01); *C10G 47/24* (2013.01); *C10G 2400/30* (2013.01)

(58) Field of Classification Search
CPC ..................................................... C10G 63/04
See application file for complete search history.

(56) References Cited

U.S. PATENT DOCUMENTS

| | | | | |
|---|---|---|---|---|
| 7,317,133 | B2 * | 1/2008 | Vora ........................ | C07C 1/20 585/324 |
| 2002/0082460 | A1 * | 6/2002 | Verduijn .................. | B01J 29/80 585/475 |
| 2010/0331590 | A1 * | 12/2010 | Majumder ............. | C10G 11/00 585/315 |
| 2014/0209509 | A1 * | 7/2014 | Hassan .................. | C10G 45/00 208/108 |
| 2015/0284646 | A1 * | 10/2015 | Fanget .................. | C10G 63/04 585/321 |

FOREIGN PATENT DOCUMENTS

WO    WO-2015128317 A1 *   9/2015   ............. C10G 63/04

\* cited by examiner

*Primary Examiner* — Philip Y Louie
*Assistant Examiner* — Alyssa L Cepluch
(74) *Attorney, Agent, or Firm* — Greer, Burns & Crain, Ltd.

(57) ABSTRACT

A naphtha cracking feed stream is taken, heated and passed to a cracking reactor. Hydrogen is added to the cracking reactor to mitigate catalyst deactivation. The aliphatic compounds are selectively cracked and at least a portion of the alkyl groups on the aromatic compounds are selectively dealkylated in the presence of a cracking catalyst to produce a cracked effluent stream comprising aromatic compounds and cracked olefins.

20 Claims, 6 Drawing Sheets

ALIPHATIC CRACKING AND DEALKYLATION WITH HYDROGEN DILUENT

CROSS-REFERENCE TO RELATED APPLICATION

This application claims priority from Provisional Application No. 62/439,337 filed Dec. 27, 2016, the contents of which cited application are hereby incorporated by reference in its entirety.

BACKGROUND

Aromatics, particularly benzene, toluene, ethylbenzene, and the xylenes (ortho, meta, and para isomers), which are commonly referred to as "BTEX" or more simply "BTX," are extremely useful chemicals in the petrochemical industry. They represent the building blocks for materials such as polystyrene, styrene-butadiene rubber, polyethylene terephthalate, polyester, phthalic anhydride, solvents, polyurethane, benzoic acid, and numerous other components. Conventionally, BTX is obtained for the petrochemical industry by separation and processing of fossil-fuel petroleum fractions, for example, in catalytic reforming or cracking refinery process units, followed by BTX recovery units.

Typically, integrated refining-petrochemical complexes separate a crude feedstock into a "straight run" or desired fraction of naphtha, such as $C_6$-$C_{10}$ naphtha, i.e., naphtha containing hydrocarbons having six to ten carbon atoms, and a heavier fraction containing longer chain hydrocarbons such as heavy oils and residues. The naphtha stream typically undergoes reforming to produce a reformate stream with an increased aromatic content. The reformate stream is processed in an aromatics complex to produce selected aromatic products, such as benzene and para-xylene.

Some of the naphtha, typically about 5-20 wt % of the $C_{5+}$ reformer feed stream remains as aliphatic $C_{5+}$ hydrocarbon in the reformate after the reforming reaction. The reformate is separated from the $C_{4-}$ components in a flash separator and a debutanizer column, and then split in a reformate splitter column between the $C_{8-}$ fraction having the majority of the aliphatics and the $C_{8+}$ fraction having a higher concentration of aromatics than the $C_{8-}$ fraction. The aliphatics are in the $C_{8-}$ fraction which are separated in an extractive unit, which commonly uses Sulfolane solvent, as a raffinate from the aromatic benzene and toluene. The benzene is further fractionated as a pure petrochemical product. The raffinate is then normally blended into gasoline or sent to a thermal cracking unit to produce ethylene, propylene, and heavier components.

The reformate splitter column and the extractive unit, which may include three columns, are expensive to build and to operate. In addition, the utilization of the raffinate stream from the extractive distillation unit rich in aliphatics or light boiling naphtha streams with T95 boiling point of less than 82° C. is often difficult for gasoline blending as it has relatively low octane number and high vapor pressure or for thermal steam cracking to convert to ethylene and propylene because it requires a large investment in a downstream cracking unit.

Therefore, there is a need for processes for converting naphtha into aromatics which reduce capacity of expensive distillation columns and improve the value of the raffinate stream and other light naphthas at lower capital cost.

SUMMARY

One aspect of the subject matter is a process for making olefins. Another aspect of the subject matter is a process for dealkylating alkylaromatics olefins. In an embodiment, the process comprises taking a cracking feed stream boiling in the naphtha range comprising aromatic compounds and aliphatic compounds, wherein at least a portion of the aromatic compounds contain alkyl groups and passing the cracking feed stream at a temperature of at least 500° C. to the cracking reactor comprising a cracking catalyst including a zeolite with a pore size greater than 5 Angstroms. The aliphatic compounds are selectively cracked and the alkyl groups on the aromatic compounds are selectively dealkylated in the presence of the cracking catalyst in the cracking reactor under cracking conditions to cracked olefins and aromatic compounds in a cracked effluent stream. We have found that providing adding at least about 60 mol % hydrogen to the cracking reactor stably preserves the cracking catalyst against deactivation. We have also found that providing at least 50 mol % hydrogen to the cracking reactor with a hydrogen partial pressure under about 345 kPa (50 psia) maintains a higher ratio of olefins to paraffins.

DETAILED DESCRIPTION

The present subject matter may involve cracking aliphatics and dealkylating alkylaromatics in a naphtha stream. A stream boiling in the naphtha range may be taken as a cracking feed stream. The naphtha stream may be reformer effluent stream. The reformer effluent stream may be taken directly to the cracking reactor without separating the reformer effluent stream into various components or a portion of the reformer effluent stream may be taken from the reformer effluent stream and fed to the cracking reactor as a cracking feed stream. The aliphatics remaining in the cracking feed stream are converted directly to at least one of ethylene, propylene, and butylene at conversion rates of 30% or more. Aliphatics are also covered to light paraffins. Furthermore, there is a concurrent increase in hydrogen and significant dealkylation of the ethyl and longer substituents on the aromatic rings. The dealkylated substituents are also converted to olefins. Under some conditions, new aromatic rings can be produced.

The process produces at least one of ethylene, propylene, and butylene from the naphtha stream. By converting aliphatics in a naphtha stream that is a reformer effluent stream, the flow rate of aliphatics in the reformate to an aromatic extractive distillation section and thermal naphtha cracker if present is reduced. The process also converts a large amount of the benzene co-boiler material, which may reduce the load on an aromatics extraction section for benzene purification. In addition, the increase in the production of aromatics will lead to higher production of combined benzene and para-xylene from the aromatics complex for a given amount of naphtha feed. Furthermore, the dealkylation of ethyl and longer aromatic substituents on the aromatic compounds from the reformer will add to the yield of light olefins and decrease the size of equipment and utilities in the aromatics complex by reducing the amount of ethylbenzene circulating in the para-xylene separation, xylene isomerization loop and reducing the amount of dealkylation required in the transalkylation reactor.

We have surprisingly found that dilution of the cracking feed with hydrogen diluent preserves a cracking catalyst against deactivation particularly when the catalyst is deficient in hydrogenation metals. The dilution enables the catalyst to crack the naphtha to olefins at high yields for extended duration on stream. By utilizing a steamed silicalite or other low acidity zeolite with a high ratio of silica to alumina as catalyst at relatively low pressure, aliphatics including saturates can crack at elevated temperature without significant deactivation or hydride transfer reactions which would cause rapid coke deposition and co-generation of heavy aromatics and paraffins rather than desired olefins.

If the process is used for reformate cracking, hydrogen is readily available, so the cracking process may be close-coupled to the reformer allowing the reformer effluent to cascade into the cracking reactor.

While this process is particularly well suited for reformate cracking where hydrogen is readily available, other configurations such as cracking naphtha, Sulfolane raffinate, FCC cracked naphtha, pentanes or other feeds containing aliphatics and combinations thereof are envisioned.

A cracking feed stream boiling in the naphtha range may be taken for the subject process. In some embodiments, the naphtha stream may have a T5 boiling point in a range of about 0° C. to about 34° C. and a T95 boiling point in a range of about 140° C. to about 215° C. In another embodiment, the naphtha stream may be split into a light naphtha stream having a T5 boiling point in a range of about 0° C. to about 34° C. and a T95 boiling point in a range of about 20° C. to about 82° C., and a heavy naphtha stream having a T5 boiling point in a range of about 20° C. to about 82° C. and a T95 boiling point in a range of about 140° C. to about 215° C. In this embodiment, the heavy naphtha stream may be taken as the cracking feed stream. As used herein, the term "T5" or "T95" means the temperature at which 5 mass percent or 95 mass percent, as the case may be, respectively, of the sample boils using ASTM D-6352.

A naphtha feed stream may be reformed to produce aromatics, such as BTX and aliphatic compounds, such as $C_5$, $C_6$ and $C_7$ branched and normal paraffins and cyclic paraffins. The term "$C_x$" or "$A_x$" are to be understood to refer to aliphatic and aromatic molecules, respectively, having the number of carbon atoms represented by the subscript "x". Similarly, the term "$C_{x-}$" or "$A_{x-}$" refers to aliphatic and aromatic molecules, respectively, that contain less than or equal to x and preferably x and less carbon atoms. The term "$C_{x+}$" or "$A_{x+}$" refers to aliphatic and aromatic molecules, respectively, with more than or equal to x and preferably x and more carbon atoms. $C_2$-$C_4$ alkyl aromatics are defined such that an alkyl aromatic that contains an alkyl chain with x carbon atoms and an additional or additional chain or chains with other numbers of carbon atoms. For example, 2-ethyltoluene is a $C_2$-$C_4$ alkyl aromatic.

A cracking feed stream may be taken from the reforming effluent stream and is heated and passed to a cracking reactor. In some embodiments, a feed stream to the reforming unit can be produced by introducing a naphtha stream to a naphtha splitter column. The naphtha stream may be split into at least two streams. In some embodiments, the naphtha stream is split into a light naphtha stream having a T5 boiling point in a range of about 0° C. to about 34° C. and a T95 boiling point in a range of about 20° C. to about 82° C., and a heavy naphtha stream having a T5 boiling point in a range of about 20° C. to about 82° C. and a T95 boiling point in a range of about 140° C. to about 215° C. The heavy naphtha stream may be sent to a naphtha hydrotreating reactor to produce a hydrotreated naphtha stream. The hydrotreated naphtha stream could then be introduced into the reforming unit. In some embodiments, the light naphtha stream from the naphtha splitter column can be sent to the cracking reactor, and the hydrocarbons in the overhead stream can be selectively cracked to produce additional olefins. However, if this is done, the naphtha hydrotreating reactor should precede the naphtha splitter to remove sulfur and nitrogen compounds which can be detrimental to the cracking catalyst at high concentrations.

In some embodiments, an additional stream having a T5 boiling point in a range of about 0° C. to about 34° C. and a T95 boiling point in a range of about 20° C. to about 82° C. can be sent to the cracking reactor. Suitable sources for the additional stream can be light naphtha from hydrotreated straight run naphtha, light naphtha from straight run naphtha, aromatics extraction raffinate, hydrocracked light naphtha, hydrotreated fluidized catalytic cracker light, heavy or full range naphtha perhaps from gas oil, or combinations thereof.

In some embodiments, the cracked olefins, comprising at least one of ethylene, propylene, and butylene, from the cracking reactor are recovered. In some embodiments, an aromatic lean fraction is sent to a downstream cracking zone to produce additional olefins, comprising at least one of ethylene, propylene, and/or butylene, which are then recovered along with the cracked olefins produced in the cracking reactor. The recovered cracked olefins and additional olefins can be fractionated to obtain ethylene and propylene streams greater than about 90 wt % pure, or greater than about 95 wt % pure, or greater than about 99 wt-% pure, or greater than about 99.5 wt-% pure.

Figure 1:
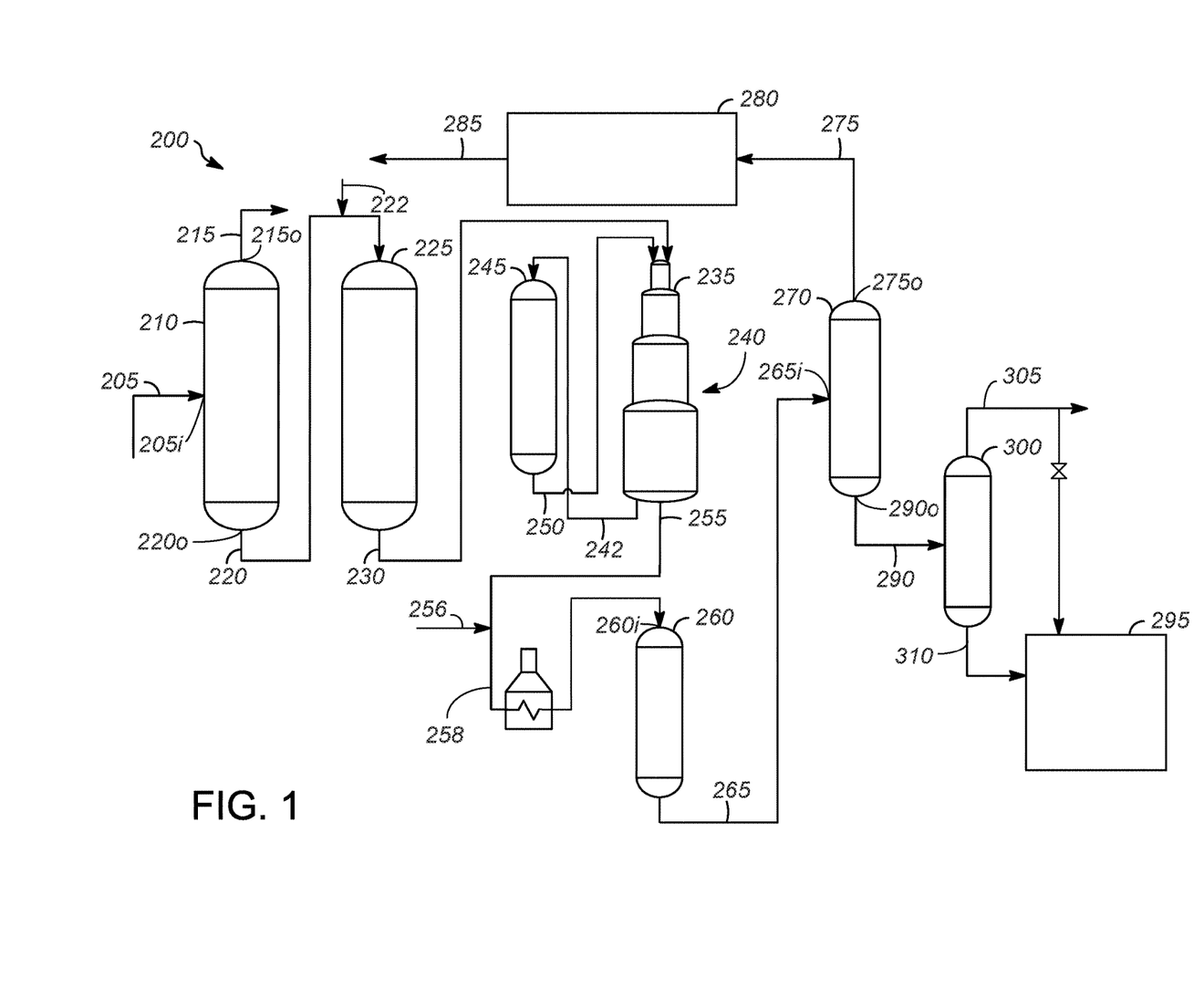
FIG. 1 is an illustration of an embodiment of a process for converting naphtha into aromatics according to the present invention.

FIG. 1 shows one embodiment of a process 200 for converting a reformed heavy naphtha stream into aromatics. The naphtha feed stream 205 is sent to a naphtha splitter column 210. The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottoms stream back to the bottom of the column. Feeds to the columns may be preheated. Unless otherwise indicated, overhead lines and bottoms lines refer to the net lines from the column downstream of any reflux or reboil to the column. Stripping columns may omit a reboiler at a bottom of the column and instead provide heating requirements and separation impetus from a fluidized inert vaporous media such as steam. The naphtha splitter column 210 has an inlet 205*i*, an overhead outlet 215*o* and a lower outlet 220*o* in a lower half of the column which may be a bottoms outlet. The naphtha feed stream 205 is separated into a light naphtha stream in a naphtha splitter overhead line 215 having a T5 boiling point in a range of about 0° C. to about 34° C. and a T95 boiling point in a range of about 20° C. to about 82° C. and a heavy naphtha stream in a naphtha splitter bottoms line 220 having a T5 boiling point in a range of about 20° C. to about 82° C. and a T95 boiling point in a range of about 140° C. to about 215° C.

The heavy naphtha stream in the naphtha splitter bottoms line 220 is sent to a naphtha hydrotreating reactor 225. The naphtha hydrotreating reactor 225 may be used to prepare the heavy naphtha stream 220 for downstream reforming with sensitive noble metal catalyst systems. In an exemplary process, the heavy naphtha stream in the naphtha splitter bottoms line 220 is mixed with hydrogen from line 222, heated to a reaction temperature and is brought into the naphtha hydrotreating reactor 225 and contacted with a hydrotreating catalyst. The naphtha hydrotreating reactor 225 may be in downstream communication with the lower outlet 220o of the naphtha splitter column 220. The term "downstream communication" means that at least a portion of material flowing to the subject in downstream communication may operatively flow from the object with which it communicates. Exemplary hydrotreating catalysts include metals from CAS Group VIB, VIIB, VIII, and combinations thereof. The naphtha hydrotreating reactor 225 may have multiple distinct stages with different catalytic zones. For example, the first stage can be operated at low temperature (e.g., about 40° C. to about 250° C.) for mainly diolefin saturation, and the second stage can be operated at higher temperature (e.g., up to about 400° C.) for olefin saturation, hydrodesulfurization, and hydrodenitrogenation. For a single stage, exemplary reaction temperatures are from about 250° C. to about 400° C. The main catalytic reactions in naphtha hydrotreating zone 225 convert the contaminants detrimental to noble metal catalyst systems, such as sulfur, nitrogen, and oxygenates, via hydrogenolysis reactions to hydrogen sulfide, ammonia, and water, so that they can be removed from the naphtha stream as gas. Metals in the bottoms stream may be removed by adsorption onto the hydrotreating catalyst. As a result, olefins and/or diolefins are also saturated.

The reforming reactor 235 may be in downstream communication with naphtha hydrotreating reactor 225. The resulting hydrotreated stream 230 contains paraffins, naphthenes and aromatics, and low levels of olefins and is fed to a reforming unit 240 for conversion of paraffins and naphthenes into aromatics. An exemplary reforming unit 240 is a catalytic reforming reactor 235 with a continuous catalyst regeneration (CCR) unit 245. The reforming reactor 235 may be operated at a temperature of from about 450° C. to about 560° C. A spent catalyst stream 242 from the bottom of the reforming reactor 235 may be sent to a top of a catalyst regenerator 245. A regenerated catalyst stream 250 from a bottom of the catalyst regenerator 245 may be sent to the top of the reforming reactor 235. Alternatively, the catalyst can be regenerated in situ by taking one of multiple reactors off-line for regeneration in cyclical fashion or in semi-regenerative mode where all reactors are taken offline for regeneration at one time.

Compounds in the hydrotreated stream 230 are reformed in the reforming reactor 235 over reforming catalyst to produce a reformer effluent stream in a reformate line 255. Specifically, naphthenes are dehydrogenated to form aromatics, normal paraffins are isomerized to form isoparaffins, and paraffins are dehydrocyclized, i.e., dehydrogenated and aromatized, to form aromatics.

A cracking feed stream may be taken from the reformer effluent stream in reformate line 255 with or without separating the reformer effluent stream 255 into different streams with different compositions. Accordingly, some or all of the reformer effluent stream in reformate line 255 may be taken by aliquot or separation by volatility or solubility as the cracking feed stream to a cracking reactor 260. The cracking feed stream may comprise the reformer effluent stream passing directly to the cracking reactor 260. By passing directly to the cracking reactor, we mean that the reformer effluent stream's composition is not changed by separation into component streams (e.g., the reformer effluent stream is not fractionated). However, the composition can be changed by adding one or more streams to the reformer effluent stream and still be considered as passing directly to the cracking reactor. In an alternative embodiment, a portion of the reformer effluent stream may be taken as the cracking feed stream and passed to the cracking reactor. The cracking feed stream may be taken by separation, flashing, distillation, extraction or by aliquot appropriation of the reformer effluent stream.

The cracking reactor 260 may be in downstream communication with the reforming reactor 235. The cracking reactor 260 may be in direct, downstream communication with the reforming reactor 235. The term "direct communication" means that flow from the upstream component enters the downstream component without passing through a fractionation or conversion unit to undergo a compositional change due to physical fractionation or chemical conversion.

In FIG. 1, all of the reformer effluent stream is taken as the cracking feed stream to the cracking reactor 260 in a cracking feed line 258. In FIG. 1, the cracking reactor 260 is in direct, downstream communication with the reforming reactor 235. The cracking feed stream enters the cracking reactor 260 through the inlet 260i.

An additional stream in line 256 which may have a T5 boiling point in a range of about 0° C. to about 34° C. and a T95 boiling point in a range of about 20° C. to about 82° C. may supplement the cracking feed stream in cracking feed line 258 and be sent to the cracking reactor 260 therewith. Consequently, the light naphtha stream in line 215 that would not benefit from reforming may bypass the reforming unit 240 and be fed to the cracking reactor 260 as the cracking feed stream.

In an embodiment, any naphtha stream boiling in the naphtha boiling range may be taken as cracking feed stream to the cracking reactor 260. The cracking feed stream may comprise $C_4$ to $C_{11}$ hydrocarbons having at least 10 wt % paraffins and at least 15 wt % alkylaromatics. The cracking feed stream may have an aromatic content of at least 30 wt %, with at least 50 wt % preferred. The feed stream may have about 5 to about 40 wt % and typically about 10 to about 25 wt % alkyl aromatics with $C_2$ to $C_4$ alkyl groups. Moreover, the cracking feed stream may have a concentration of aromatic alkyl groups in the $C_1$-$C_4$ range of about 10 to about 30 wt % and preferably about 15 to about 25 wt %. At least 10 wt %, preferably at least 15 wt % of the aromatic alkyl groups in the feed stream may comprise $C_1$-$C_4$ alkyl groups. The cracking feed stream may have about 5 to about 40 wt %, preferably 10 to 30 wt % aliphatics in the $C_5$ to $C_9$ range. The cracking feed stream need not comprise olefins.

The cracking feed stream in the cracking feed line 258 may be heated to at least 500° C. if it is not already at reactor temperature and passed to the cracking reactor 260. The cracking feed stream in the cracking feed line 258 may be cracked over an acidic cracking catalyst to produce cracked olefins comprising at least one of ethylene, propylene, and butylene, methane, ethane, propane, butane and dealkylated aromatics. Typically, substantial yields of ethylene, propylene and butylene are produced in the cracking reactor. Substantial yields means at least 5 wt %, suitably at least 10 wt % and preferably at least 20 wt % of ethylene, propylene and butylene combined. "Yield" in this case is defined as the weight of the product component in the cracked effluent stream, divided by the combined weight of aliphatics and the alkyl-aromatic side chains in the feed. Accordingly, the aromatic rings are not counted as feed in the yield calculation.

Examples of suitable cracking reactors include, but are not limited to, fixed bed reactors, moving bed reactors, fluidized bed reactors, and ebullated bed reactors. For example, the reactors could be a series of multiple reactors with interstage heating. In a moving bed reactor, the cracking catalyst is contacted with the cracking feed stream while slowly moving from a top of the cracking reactor 260 to a bottom of the cracking reactor where it is taken to a catalyst regenerator for regeneration and returned to the top of the cracking reactor. The cracking reactor may comprise an interstage heater to maintain reactor temperature. The acid catalyst may be continuously regenerated, for example in a continuous catalyst regenerator. A swing bed reactor may also be used for a cracking reactor that uses a fixed bed of catalyst.

The cracking catalyst may include a zeolite that has one of the MFI, TON, MTT, FER, EUO or FAU framework. The preferred zeolite has an MFI type framework. The catalyst does not include a hydrogenating metal function. For example, the catalyst may have 0 to about 0.1 wt-% transition metals in IUPAC Groups 5 to 12 on the Periodic Table on the catalyst, with zero being preferred. The absence of such hydrogenating transition metals assures that olefins will not be hydrogenated in the cracking reactor to preserve olefins, particularly when substantial hydrogen is present. Catalysts may be of many formulations including pure zeolites, or formed catalysts such as extruded, oil dropped, or spray dried catalysts. Suitable catalysts may also contain silica, aluminum, phosphate, alumina, zirconia, titania or other binders which do not have a hydrogenation function. A suitable cracking catalyst includes, but is not limited to, a ZSM-5 zeolite. For example, a silicalite can be used.

The cracking catalyst should have an acidic functionality in order to crack aliphatic molecules and dealkylate alkylaromatics. In some embodiments, the cracking catalyst may have a molar ratio of silica to alumina in the zeolite of about 200 to about 1200, suitably about 300 to about 1100, typically no more than about 700, and preferably between about 300 and about 500. The cracking catalyst particles should include a zeolite having a maximum pore diameter of greater than 5 Angstroms. For example, the maximum pore diameter should be at least 5.1 Angstroms and preferably at least 5.3 Angstroms. Moreover, it is preferred that the zeolite have a minimum pore diameter of at least 5.1 Angstroms. A maximum pore diameter of more than 8 Angstroms would not be desirable. Preferably, the pore index should be at least about 28 Angstroms. More than 90 wt % and preferably at least 95 wt % of the catalyst particles in the reactor should include a zeolite with the foregoing pore diameter specifications to promote dealkylation of alkyl groups from aromatic rings. The catalyst particles may include 30 to 80 wt % zeolite with the remaining support and binder being non-zeolitic and/or low-acidic. Low acidic binder has no more than 0.2, preferably no more than 0.15 millimoles of acid sites per gram as determined by gas-phase ammonia titration.

The cracking feed temperature should at least be about 500° C. when passed to the reactor. The temperature in the cracking reactor may be in the range of about 500° C. to about 700° C., or about 525° C. to about 650° C. and preferably about 5350 to about 590° C. Temperature in the reactor refers to the weight average bed temperature which is the average of the bed temperature taken at the inlet and the outlet of the catalyst bed and evenly spaced intervals between an inlet and an outlet of the bed. The pressure can be of about 0 kPa (gauge) (0 psig) to about 750 kPa (g) (109 psig), or about 100 kPa (g) (15 psig) to about 400 kPa (g) (58 psig). The molar ratio of hydrogen to $C_{5+}$ hydrocarbon at the inlet 260i to the cracking reactor may be at least about 0.5:1, or at least about 1:1, preferably at least about 2:1 and no more than about 6:1, and most preferably no more than about 5:1. The hydrogen may be provided from the reformate stream 255. The reaction conditions include a weight hourly space velocity (WHSV) in the range of about 0.75 to about 6.0 $hr^{-1}$, suitably no more than about 4 $hr^{-1}$, preferably no more than about 3.75 $hr^{-1}$ and preferably no more than about 3.0 $hr^{-1}$. The term "WHSV is defined as the mass flow rate of liquid feed divided by the mass of the catalyst. The liquid hourly space velocity (LHSV) in the cracking reactor may be between about 0.1 to about 4.0 $hr^{-1}$ and preferably about 0.5 to about 2 or about 2.5 $hr^{-1}$. The term "LHSV" is defined herein as the volumetric flow rate of feed divided by the volume of the catalyst bed. The relationship between LHSV and WHSV depends on the feed density and the catalyst apparent bulk density.

In some embodiments, at least a portion of the ethyl and larger alkyl groups on the aromatic compounds are dealkylated in the cracking reactor to produce additional olefins, comprising at least one and typically substantial yields of ethylene, propylene, and butylene, and a dealkylated aromatic compound. Demethylation of aromatic rings are undesirable.

We have found that $A_6$-$A_{10}$ are generated in the cracking reactor in many cases in addition to aromatic products resulting from dealkylation of alkyl aromatics. These conditions will be such that at least about 50 to about 80 wt-% of aliphatics will be converted and at least about 50 to about 80 wt-% of the $C_2$-$C_4$ alkyl aromatics will be dealkylated to the corresponding light olefin and aromatics. Aromatic $C_1$-$C_4$ alkyl groups are dealkylated to olefins and aromatics at over 10% by weight, but aromatic $C_2$-$C_4$ alkyl groups are dealkylated at over 50% by weight, and typically at over 60% by weight. Aromatic $C_1$ alkyl groups are converted at less than about 10% by weight, typically at less than about 6% by weight and preferably less than about 3% by weight. Altogether, $C_{5+}$ aliphatics and aromatic alkyls groups are converted at over 40%. Preferably, $C_{5+}$ aliphatic conversion is about 50 to about 80% by weight. At higher conversion olefin selectivity decreases.

The aliphatic compounds in the cracking feed stream are selectively cracked to produce cracked olefins, including at least one and typically substantial yields of ethylene, propylene, and butylene. Due to the lack or low concentration of hydrogenating, transition metal on the catalyst, the olefin to paraffin weight ratio of $C_1$-$C_4$ hydrocarbons in the cracking effluent stream may be at least 0.1 and typically at least 0.25 and suitably at least about 0.7, preferably at least about 1, and in some exemplary embodiments at least about 1.8. The cracking effluent stream from the cracking reactor contains dealkylated aromatics that were alkylaromatics from the reformer effluent stream or cracking feed stream and olefins dealkylated from aromatics and cracked from paraffins in the cracking reactor, as well as paraffins and hydrogen. Alkyl groups may also be transferred from one aromatic molecule to another, effecting transalkylation.

Surprisingly, we found hydrogen in the reactor helps to stabilize the catalyst against deactivation by coke formation even without a hydrogenation metal present. This effect is not observed when using other gases as diluent, like nitrogen or steam. We observed stable aliphatic conversion of over 90 wt % for extended periods with little catalyst deactivation with hydrogen concentration of at least 60 mol % in the cracking reactor. Hydrogen concentration of at least 70 mol % would be suitable and at least 80 mol % would be preferable. Hydrogen concentration should not exceed 90 mol % in the cracking reactor. The mole ratio of hydrogen to hydrocarbon should be at least 2, suitably at least 3 and preferably at least 4. The mole ratio of hydrogen to hydrocarbon should not exceed 6.

We have observed at lower pressure, more olefins, fewer paraffins and fewer aromatics are produced. At high pressures of about 253 kPa (absolute) (65 psia) to about 448 kPa (115 psia), olefin yield is lower and yields of propane, ethane, methane and aromatics is higher. We observed that higher pressures provided longer effective residence time which led to more extensive reaction of olefins to aromatics. We also observed high light paraffin yield at higher pressures indicating that some hydrogenation may occur at high hydrogen partial pressure. Consequently, hydrogen partial pressure greater than about 345 kPa (absolute) (50 psia) should be avoided. Despite the presence of hydrogen, olefins do not substantially hydrogenate back to form paraffins in the hydrogen partial pressure range of no more than 345 kPa (absolute) (50 psia) enabling a light olefin-to-paraffin ratio of at least 0.7. With hydrogen mol % of at least 50, a hydrogen partial pressure range of no more than 345 kPa (absolute) (50 psia) enables achievement of a light olefin-to-paraffin ratio of at least 0.6 With hydrogen mol % of at least 60, a hydrogen partial pressure range of no more than 345 kPa (absolute) (50 psia) enables achievement of a light olefin-to-paraffin ratio of at least 1.0. A hydrogen partial pressure range of no more than 241 kPa (absolute) (35 psia) enables achievement of a light olefin-to-paraffin ratio of at least about 1.8, provided that the residence time is less than about 6 seconds to prevent conversion of olefins to aromatics.

Hydrogen partial pressure should be maintained above 62 kPa (absolute) (9 psia). Low conversion and fast deactivation are observed in the presence of steam, but high conversion and no deactivation are observed in the presence of hydrogen.

Stated differently, hydrogen may be used as a co-feed diluent with a mole ratio of hydrogen to hydrocarbon of at least 2 and a hydrogen partial pressure between about 138 kPa (absolute) (20 psia) and about 345 kPa (absolute) (50 psia) with a total pressure of at least about 207 kPa (absolute) (30 psia) or with a hydrogen partial pressure of at least about 62 kPa (absolute) (9 psia) with total pressure between about 69 kPa (absolute) (10 psia) and 207 kPa (absolute) (30 psia).

A cracked effluent stream from the cracking reactor 260 in a cracked effluent line 265 may be cooled and separated into an aromatic rich stream and an aromatic lean stream by fractionation. By aromatic rich stream, we mean a stream containing at least about 90 wt % aromatic compounds, or at least about 95 wt %, or at least about 97 wt %, or at least about 99 wt %. By aromatic lean stream, we mean a stream containing less than about 30 wt % aromatic compounds, or less than about 20 wt %, or less than about 10 wt %. The cracked reformer effluent stream in a cracked effluent line 265 comprising the aromatics and the olefins may be sent to an aromatics fractionation column 270, for example a depentanizer or debutanizer column, from which an aromatics lean stream comprising $C_{4-}$ or a $C_{5-}$ stream in an aromatics overhead line 275 is removed. The aromatics fractionation column may be a vapor-liquid separator. As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

The aromatics fractionation column 270 has an inlet 265i, an overhead outlet 275o, and a lower outlet 290o in the bottom half of the column which may be a bottoms outlet. The inlet 265i of the aromatics fractionation column 270 may be in downstream communication with the cracking reactor 260.

The aromatic rich stream can be recovered from the lower outlet 290o in aromatics bottoms line 290 and used to produce benzene and/or para-xylene. In some embodiments, the aromatic rich stream can be passed directly to an aromatics complex 295 without subjecting the aromatic rich stream to a distillation column or other separation process. In other embodiments, the aromatic rich stream is fractionated in a reformate splitter column 300 into at least a reformate splitter overhead stream comprising $C_{6-}$ or $C_{7-}$ hydrocarbons in a reformate splitter overhead line 305 that may be forwarded to a gasoline pool perhaps after isomerization and a reformate splitter bottoms stream comprising $C_{7+}$ or $C_{8+}$ hydrocarbons in a reformate splitter bottoms line 310 that may be forwarded to the aromatics complex 295. In some embodiments, both the reformate splitter overhead stream and the reformate splitter bottoms stream may be delivered to the aromatics complex 295. In an aspect, at least 50 wt %, or at least about 60 wt %, or at least about 70 wt %, or at least about 75 wt %, or at least about 80 wt %, or at least about 85 wt %, or at least about 90 wt %, or at least about 95 wt % of the aromatics rich stream in the aromatics bottoms line 290 may be sent to the aromatics complex 295.

A downstream cracking reactor 280 may be in downstream communication with the overhead outlet 275o of the aromatics fractionation column 270. Hydrogen and light gases may be removed from the aromatics lean stream in the aromatics overhead line 275 upstream of the downstream cracking reactor 280. The overhead stream in the overhead line 275 may be sent to a downstream cracking reactor 280, with or without removing the produced olefins before the downstream cracking reactor, such as a steam cracker where it is cracked to produce additional olefins comprising at least one and typically substantial amounts of ethylene, propylene, and/or butylene. A downstream cracked stream 285 comprises the cracked olefins from the cracking reactor 260 and the additional olefins produced in the downstream cracking reactor 280, and heavier components. The aromatics complex 295 may be in downstream communication with the lower outlet 290o of the fractionation column 270.

Figure 2:
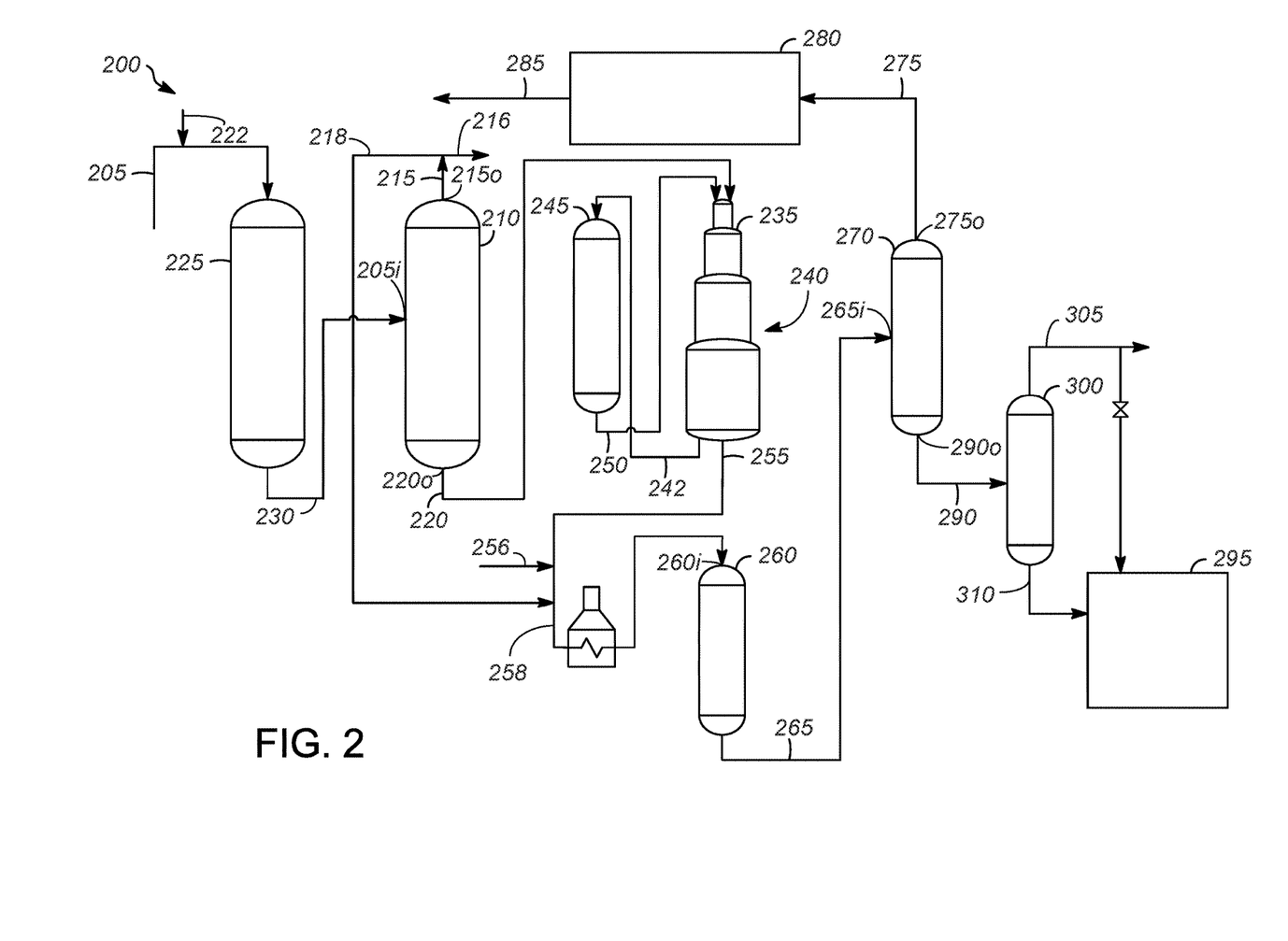
FIG. 2 is another embodiment of a process for converting naphtha into aromatics according to the present invention.

FIG. 2 is similar to FIG. 1, except that the naphtha feed stream in naphtha feed line 205 is mixed with hydrogen from hydrogen line 222 and sent to the naphtha hydrotreating reactor 225 before a hydrotreated naphtha stream in a hydrotreater effluent line 230 is fed from the naphtha hydrotreating reactor 225 to the naphtha splitter column 210 through an inlet 205i. The hydrotreated naphtha stream in a hydrotreater effluent line 230 is sent to the naphtha splitter column 210 in which it is separated into a hydrotreated light naphtha stream in a naphtha splitter overhead line 215 from an outlet 215o having a T5 boiling point in a range of about 0° C. to about 34° C. and a T95 boiling point in a range of about 20° C. to about 82° C. and a hydrotreated heavy naphtha stream in a naphtha splitter bottoms line 220 from a lower outlet 220o having a T5 boiling point in a range of about 20° C. to about 82° C. and a T95 boiling point in a range of about 140° C. to about 215° C. The hydrotreated bottoms stream 220 may be sent to the reformer 235.

The hydrotreated light naphtha stream in the naphtha splitter overhead line 215 may be split between a recovered portion stream in line 216 that may be further processed or used as product and an advance portion stream in an advance line 218. The advance portion stream may be advanced in advance line 218 to be mixed with a reformer effluent stream in a reformate line 255. The inlet 205i of the naphtha splitter column 210 may be in downstream communication with the naphtha hydrotreating reactor 225. Moreover, in FIG. 2 a light naphtha stream in the advance line 218 is mixed with the reformer effluent stream in the reformate line 255 to provide the cracking feed stream in the cracking feed line 258. Consequently, at least a portion of the overhead stream in the overhead line 215 may be passed to the cracking reactor 260 in which hydrocarbons from the overhead stream are selectively cracked and dealkylated. With these exceptions, everything else in FIG. 2 is the same as described for FIG. 1.

As will be understood by those of skill in the art, the figures do not show all of the equipment involved in these processes. There may be heat exchanger, coolers, flash drums, other component separators such as membranes or adsorbent, compressors, or pumps and the like between the various pieces of equipment that are shown.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

EXAMPLES

The catalyst used in Examples 1-8 was an extruded catalyst prepared from 70 wt % silicalite zeolite with a ratio of silica to alumina of 460 and 30 wt % silica binder. The extruded catalyst was dealuminated, calcined and depleted of alkali metal. The finished catalyst had a BET surface area of 313 m$^2$/g and micropore volume of 0.14 cc/g as determined by nitrogen adsorption. The finished catalyst including binder had 30 wppm sodium, 0.17 wt % aluminum, 46.8 wt % silicon analyzed by inductively coupled plasma-atomic emission spectroscopy.

Example 1

Figure 3:
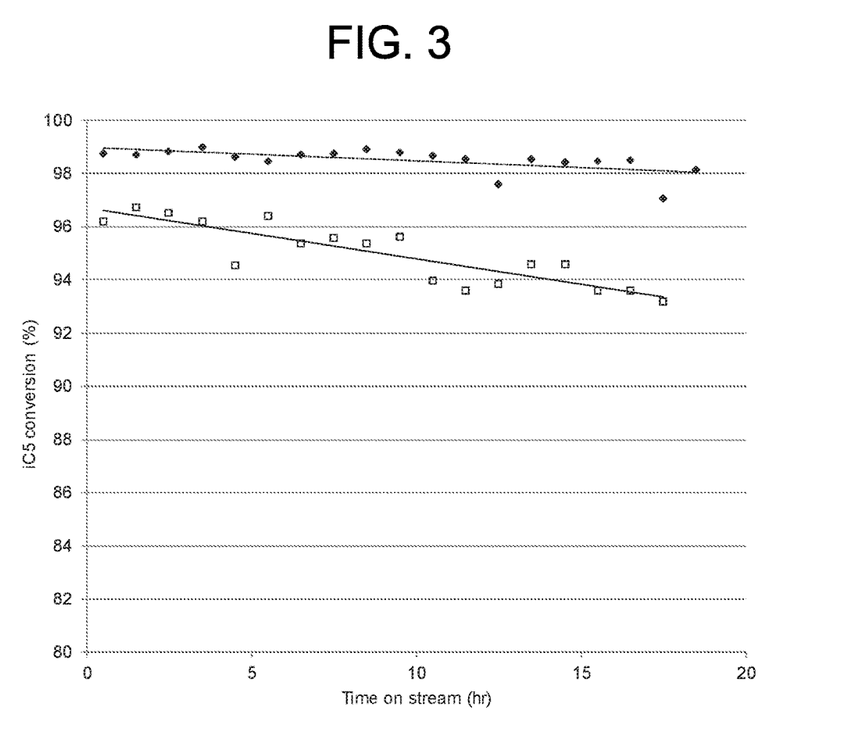
FIG. 3 is a plot of $iC_5$ conversion versus time on stream.

The silicalite catalyst was ground and sized to 40×60 mesh. Two grams of the catalyst was loaded in a 9 mm quartz reactor. The reactor was operated at atmospheric pressure and at 600° C. Pure isopentane (iC$_5$) was fed at 0.029 mL/min and vaporized at 190° C. into a vortex mixer where the vapor was mixed with a gas mixture containing 67 mol % nitrogen and 33 mol % hydrogen flowing at 15 standard cc/min. The resulting weight space velocity was 0.54 hr$^{-1}$ and the space time was 3.1 seconds. Space time was calculated as the volume of the catalyst bed over the gas volumetric flow rate. Hydrocarbon partial pressure was 27 kPa (4 psig). The product mixture was analyzed as vapor by gas chromatography. In this example, the vapor feed mixture contained 27 mol % isopentane, 24 mol % hydrogen and 49 mol % nitrogen. Initial isopentane conversion was 96.5% on average for the first 3 hours and decreased throughout the run at a rate of 0.19% conversion per hour as shown by the squares in FIG. 3. Product selectivities for hours 1 through 5 are shown in Table 1.

Example 2

The silicalite catalyst was ground and sized to 40×60 mesh. Two grams of the 70% zeolite catalyst was loaded in a 9 mm quartz reactor. The reactor was operated at atmospheric pressure and at 600° C. Pure isopentane was fed at 0.029 mL/min and vaporized at 190° C. into a vortex mixer where the vapor was mixed with a gas mixture containing 100 mol % hydrogen flowing at 15 standard cc/min. The resulting weight space velocity was 0.54 hr$^{-1}$ and the space time was 3.1 seconds. The hydrocarbon partial pressure was 76 kPa (11 psig). The product mixture was analyzed as vapor by gas chromatography. In this example, the vapor feed mixture contained 27 mol % isopentane and 73 mol % hydrogen. Initial isopentane conversion was 98.8% on average for the first 3 hours and decreased throughout the run at a rate of 0.05% conversion per hour as shown by the diamonds in FIG. 3. The increased presence of hydrogen diminished deactivation of the catalyst. Product selectivities for hours 1 through 5 are shown in Table 1.

TABLE 1

| Selectivity (wt %) | Example 1 | Example 2 |
|---|---|---|
| Methane | 9.3 | 11.4 |
| Ethane | 3.5 | 4.4 |
| Ethylene | 24.8 | 24.6 |
| Propane | 3.7 | 4.2 |
| Propylene | 26.9 | 24.6 |
| Butanes | 3.6 | 3.6 |
| Butylenes | 10.0 | 8.5 |
| C$_5$'s | 2.1 | 1.1 |
| C$_6$-C$_7$ aliphatics | 0.0 | 0.7 |
| Benzene | 5.7 | 6.4 |
| Toluene | 7.2 | 7.2 |
| Xylenes | 2.5 | 2.5 |
| Ethylbenzene | 0.5 | 0.5 |
| Other | 0.2 | 0.2 |

Examples 3-6

Examples 3-6 were run using the same silicalite catalyst as examples 1 and 2, but without grinding and sieving. The unground catalyst has apparent bulk density of 0.667 g/cm$^3$. Sixty cubic centimeters (40.0 g) of the catalyst were loaded in a fixed bed reactor in three separate catalyst plugs of 15, 15 and 30 cubic centimeters separated by quartz wool and spherical alpha alumina filler. A reformate feed with the composition shown in Table 2 and specific gravity of 0.829 g/cm$^3$ was vaporized and mixed with hydrogen. Liquid and vapor products were separated at the reactor outlet which was maintained at 172 kPa (g) (25 psig). The gas and liquid products were analyzed separately by gas chromatography.

TABLE 2

Reformate Feed

| Component | Wt % |
|---|---|
| $C_1$ Paraffin | 0.000 |
| $C_2$ Paraffins | 0.000 |
| $C_3$ Paraffins | 0.080 |
| $C_4$ Paraffins | 0.780 |
| $C_5$ Paraffins | 2.350 |
| $C_6$ Paraffins | 8.170 |
| $C_7$ Paraffins | 3.670 |
| $C_8$ Paraffins | 0.940 |
| $C_5$ Naphthenes | 0.040 |
| $C_6$ Naphthenes | 0.170 |
| $C_7$ Naphthenes | 0.180 |
| $C_8$ Naphthenes | 0.100 |
| $C_{5+}$ Aliphatics | 17.7 |
| $C_{9+}$ Paraffins, Naphthenes and Olefins | 0.210 |
| Ethylene | — |
| Propylene | — |
| $C_4$ Olefins | 0.000 |
| $C_5$ Olefins | 0.000 |
| $C_6$ Olefins | — |
| $C_7$ Olefins | 1.230 |
| $C_8$ Olefins | — |
| Benzene | 2.790 |
| Toluene | 19.340 |
| Xylene | 27.040 |
| Ethylbenzene | 3.760 |
| Trimethylbenzene | 12.510 |
| Methyl-Ethyl-Benzene | 7.960 |
| Propyl-Benzene | 1.810 |
| Tetra-Methyl Benzene | 1.420 |
| Di-Methyl-Ethyl Benzene | 2.100 |
| Methyl-Propyl-Benzene | 0.880 |
| Di-Ethyl-Benzene | 0.240 |
| Butyl-Benzene | 0.110 |
| $C_{11+}$ Aromatics | 1.450 |
| Aromatic Alkyls[a] | 23.2 |
| Aromatic $C_2$-$C_4$ Alkyls[a] | 4.3 |

[a]Aromatic alkyls counted the weight of aromatic alkyl substituents assuming molecular weights of 56.11 g/mol for butyl, 42.08 g/mol for propyl, 28.05 g/mol for ethyl and 16.04 g/mol for methyl substituents.

Example 3

Figure 4:
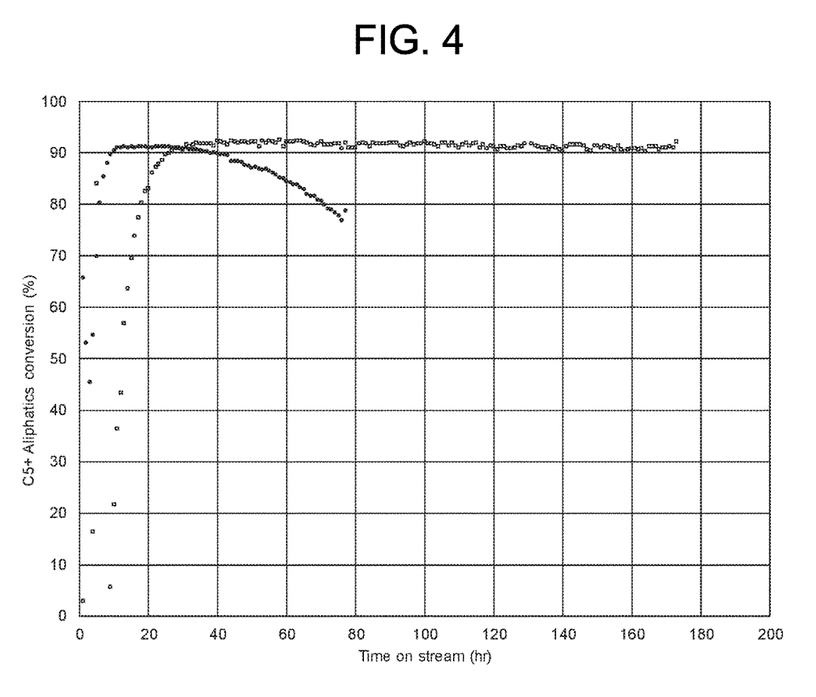
FIG. 4 is a plot of $C_{5+}$ aliphatics conversion versus time on stream.

In this example, the liquid feed rate was 60 cc/hr (49.74 g/hr), and the mole ratio of hydrogen to feed was 1:1, corresponding to a hydrogen mol % of 50 and a hydrogen partial pressure of 138 kPa (20 psia) with a total pressure of 276 kPa (40 psia). The space time in the catalyst bed was 8.4 seconds and the WHSV was 1.24 $hr^{-1}$. Feed to the reactor was cut in at 425° C. and the temperature was ramped to 600° C., reaching reaction temperature at 5 hours on stream. As shown by the solid circles in FIG. 4, aliphatic conversion reached 91 wt % at 11 hours on stream and remained constant until 40 hours on stream, corresponding to 35 bed volumes of liquid feed at reaction temperature, after which conversion began to drop. Between 41 hours on stream and the end of the run at 76 hours on stream, aliphatic conversion dropped to 75 wt % constituting an average deactivation rate of 0.36 wt % conversion lost per hour.

Example 4

In this example, the liquid feed rate was 30 cc/hr (24.9 g/hr), and the mole ratio of hydrogen to feed was 4.5:1, corresponding to a hydrogen mol % of 82 and a hydrogen partial pressure of 228 kPa (33 psia) with a total pressure of 276 kPa (40 psia). The space time in the catalyst bed was 6.1 seconds and the WHSV was 0.62 $hr^{-1}$. Feed to the reactor was cut in at 425° C. and the temperature was ramped to 600° C., reaching reaction temperature at 5 hours on stream. As shown by the hollow squares in FIG. 4, aliphatic conversion reached 91 wt % at 31 hours on stream and remained constant until the run was stopped at 173 hours on stream, corresponding to 84 bed volumes of liquid feed at reaction temperature. From 31 to 173 hours on stream the average deactivation rate was 0.009% conversion lost per hour.

Example 5

Experiments were run under conditions, feed and experimental set-up similar to Example 3 at various pressures to obtain product yields in the first 10-20 hours of a reaction at various total pressures. For all runs, the reaction temperature was 600° C., the mole ratio of hydrogen to hydrocarbon feed was 1:1 corresponding to a hydrogen mol % of 50 and the WHSV was 1.24 $hr^{-1}$. Conditions and results for the four runs are given in Table 3.

Conversion was determined by the difference in component in the product and the feed in weight percent and dividing the difference by the component in the feed in wt %. Specifically, conversion of aliphatics was determined by summing aliphatics in the feed and summing the aliphatics in the gas and liquid products in weight percent and dividing the difference by aliphatics in the feed in weight percent. Aromatic alkyl group conversion was calculated by determining the amount of each aromatic component in mol/100 g, and then converted to weight percent by multiplying each aromatic component by the molar mass of the aromatic alkyl group (or groups). Aromatic alkyl groups are counted assuming molecular weights of 56.11 g/mol for butyl, 42.08 g/mol for propyl, 28.05 g/mol for ethyl and 16.04 for methyl. For determining $C_1$-$C_4$ aromatic alkyl group conversion the conversions of aromatic methyl, ethyl, propyl and butyl groups were summed. $C_{5+}$ aliphatic and aromatic alkyls conversion was determined by the difference in $C_{5+}$ aliphatic and $C_1$-$C_4$ aromatic alkyls in the product and the feed in weight percent and dividing the difference by the $C_{5+}$ aliphatic and aromatic alkyls in the feed in weight percent.

Yields were calculated by dividing the difference of a particular product component in the product less the particular product in the feed in wt % by the amount of $C_{5+}$ aliphatics and aromatic side chains in the feed in wt %. Aromatic side chains were counted assuming molecular weights as given above. Aromatic side chains are the same as aromatic alkyl groups. The $C_{4-}$ olefin/paraffin ratio was determined by: calculating selectivities for each $C_{4-}$ olefin and paraffin by dividing yield in wt % for that component by $C_{5+}$ aliphatic and aromatic alkyls conversion, adding the selectivities for $C_{4-}$ olefins and for $C_{4-}$ paraffins and taking their ratio of the sums.

Aromatic ring balance was the ratio of the difference of the $C_6$-$C_{10}$ aromatics in the effluent and the $C_6$-$C_{10}$ aromatics in the feed in mol/100 g to the $C_6$-$C_{10}$ aromatics in the feed in mol/100 g. In these calculations, hydrogen gas diluent was not considered in the component weight and mol percentages.

TABLE 3

| | Run | | | | |
|---|---|---|---|---|---|
| | 1 | 2 | 3 | 4 | 5 |
| Pressure, kPa (psia) | 793 (115) | 448 (65) | 276 (40) | 172 (25) | 276 (40) |
| Hydrogen partial pressure, kPa (psia) | 396 (57) | 223 (32) | 137 (20) | 86 (12) | 137 (20) |
| Residence Time (sec) | 24.1 | 13.6 | 8.4 | 5.2 | 16.7 |
| Conversion | | | | | |
| $C_{5+}$ Aliphatics | 98.2 | 89.4 | 89.5 | 77.1 | 82.1 |
| Aromatic Methyl | 8.2 | 2.3 | 2.1 | 0.0 | 5.1 |
| Aromatic Ethyl | 65.5 | 46.6 | 64.3 | 46.2 | 63.3 |
| Aromatic Propyl | 82.2 | 82.1 | 84.6 | 81.1 | 86.3 |
| Aromatic Butyl | 96.1 | 90.2 | 93.2 | 86.9 | 93.8 |
| $C_1$-$C_4$ Aromatic Alkyls | 20 | 12 | 15 | 10 | 17 |
| $C_2$-$C_4$ Aromatic Alkyls | 69 | 54 | 69 | 54 | 68 |
| $C_{5+}$ Aliphatic and $C_1$-$C_4$ Aromatic Alkyls | 53.6 | 45.5 | 47.0 | 39.1 | 45.2 |
| Yields | | | | | |
| Methane | 13.2 | 7.8 | 6.0 | 3.7 | 7.8 |
| Ethane | 11.1 | 6.5 | 4.7 | 2.8 | 8.0 |
| Ethylene | 2.8 | 5.6 | 8.5 | 8.6 | 7.5 |
| Propane | 9.2 | 6.1 | 5.2 | 2.8 | 5.7 |
| Propylene | 2.4 | 5.9 | 8.5 | 10.7 | 8.6 |
| Butanes | −0.1 | 0.7 | 1.0 | 0.6 | 0.8 |
| Butylenes | 0.8 | 2.3 | 3.1 | 4.1 | 3.3 |
| $C_6$-$C_{10}$ rings | 8.1 | 7.0 | 6.7 | 3.4 | 0.7 |
| $C_{11}+$ | 6.6 | 3.8 | 3.0 | 2.2 | 3.4 |
| $C_1$-$C_4$ olefin | 6.0 | 13.8 | 20.2 | 23.4 | 19.3 |
| $C_1$-$C_4$ paraffin | 33.3 | 21.0 | 16.9 | 9.9 | 22.4 |
| Ratios and Ring Balance | | | | | |
| $C_4$-olefin/paraffin ratio | 0.18 | 0.65 | 1.19 | 2.37 | 0.87 |
| $C_6$-$C_{10}$ aromatic ring balance | 105.6 | 104.9 | 104.7 | 102.3 | 100.5 |

Example 6

Experiments were run under conditions and experimental set-up similar to Example 4 at various pressures to obtain product yields in the first 10-20 hours of a reaction at various total pressures. For all runs, the reaction temperature was 575° C., the mole ratio of hydrogen to hydrocarbon feed was 4.5:1 corresponding to a hydrogen mol % of 82. The lower temperature than in Example 5 was designed to increase olefin selectivity at the expense of producing less aromatics. Conditions for the four runs are given in Table 3. Calculations were made as in Example 5.

TABLE 4

| | Run | | | |
|---|---|---|---|---|
| | 6 | 7 | 8 | 9 |
| Pressure, kPa (psia) | 793 (115) | 345 (50) | 276 (40) | 276 (40) |
| Hydrogen partial pressure, kPa (psia) | 647 (94) | 280 (41) | 224 (33) | 224 (33) |
| WHSV ($hr^{-1}$) | 1.24 | 0.62 | 0.62 | 1.24 |
| Residence Time (sec) | 9.0 | 7.8 | 6.3 | 3.1 |
| Conversion | | | | |
| $C_{5+}$ Aliphatics | 87.3 | 85.1 | 84.8 | 74.4 |
| Aromatic Methyl | 8.2 | 2.3 | 2.1 | 0.0 |
| Aromatic Ethyl | 65.5 | 46.6 | 64.3 | 46.2 |
| Aromatic Propyl | 82.2 | 82.1 | 84.6 | 81.1 |
| Aromatic Butyl | 96.1 | 90.2 | 93.2 | 86.9 |
| $C_1$-$C_4$ Aromatic Alkyls[a] | 16 | 17 | 17 | 14 |
| $C_2$-$C_4$ Aromatic Alkyls[a] | 66 | 69 | 70 | 64 |
| $C_{5+}$ Aliphatics and $C_1$-$C_4$ Aromatic Alkyls | 46.7 | 46.4 | 46.4 | 40.0 |

TABLE 4-continued

| | Run | | | |
|---|---|---|---|---|
| | 6 | 7 | 8 | 9 |
| Yields | | | | |
| Methane | 7.3 | 6.1 | 5.5 | 3.3 |
| Ethane | 7.7 | 4.8 | 4.2 | 2.5 |
| Ethylene | 5.6 | 9.7 | 11.0 | 10.2 |
| Propane | 9.9 | 6.1 | 5.5 | 3.3 |
| Propylene | 6.0 | 10.5 | 12.0 | 12.5 |
| Butanes | 6.0 | 4.4 | 3.8 | 3.5 |
| Butylenes | 2.4 | 3.9 | 4.1 | 4.5 |
| $C_6$-$C_{10}$ rings | 1.9 | 0.3 | −0.4 | −0.1 |
| $C_{11}+$ | 0.9 | 1.2 | 1.1 | 0.2 |
| $C_1$-$C_4$ olefin | 14.0 | 24.0 | 27.0 | 27.3 |
| $C_1$-$C_4$ paraffin | 30.9 | 21.3 | 19.1 | 12.7 |
| Ratios and Ring Balance | | | | |
| $C_4$-olefin/paraffin ratio | 0.45 | 1.13 | 1.42 | 2.14 |
| $C_6$-$C_{10}$ aromatic ring balance | 105.6 | 104.9 | 104.7 | 102.3 |

As shown in Tables 3 and 4, at lower pressure and thus lower hydrogen partial pressure produced more olefins, fewer paraffins and fewer aromatics. At high pressures of 253 kPa (absolute) (65 psia) to about 448 kPa (115 psia), olefin yield is lower and yields of propane, ethane, methane and aromatics are higher.

A portion of this effect is due to longer effective residence time at higher pressure leading to more extensive reaction of olefins to aromatics. However, the high light paraffin yield indicates that some hydrogenation may occur at high hydrogen partial pressure, so hydrogen partial pressure greater than about 345 kPa (absolute) (50 psia) should be avoided.

Despite the presence of hydrogen, olefins do not substantially hydrogenate back to form paraffins in the hydrogen partial pressure range of no more than 345 kPa (absolute) (50 psia) enabling a light olefin-to-paraffin ratio of at least 0.6. With hydrogen mol % of at least 60, hydrogen partial pressure range of no more than 345 kPa (absolute) (50 psia) enables a light olefin-to-paraffin ratio of at least 1.0.

Aromatic $C_6$-$C_{10}$ ring balance of over 100% indicates that aromatics are being generated in the cracking reactor. $C_{5+}$ aliphatics were converted at over 70%. Aromatic $C_1$-$C_4$ alkyl groups were dealkylated to olefins and aromatics at over 10%, but aromatic $C_2$-$C_4$ alkyl groups were dealkylated at over 50%, and over 60% in some examples. Altogether, $C_{5+}$ aliphatics and aromatic alkyls were converted to produce light olefins at over 40%.

Example 7

Figure 5:
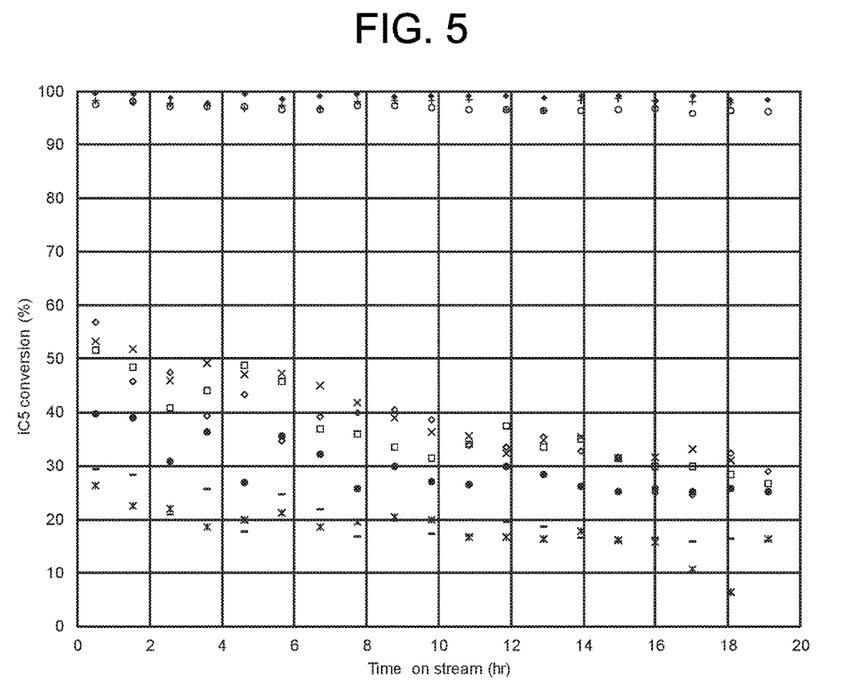
FIG. 5 is a plot of $iC_5$ conversion versus time on stream.

The silicalite catalyst was ground and sized to 40×60 mesh. Two grams of the catalyst was loaded in a 9 mm quartz reactor. The catalyst was pretreated in nitrogen for 2 hours at 550° C. The reactor was operated at atmospheric pressure. Pure isopentane was fed to the reactor in vapor phase along with steam and/or hydrogen. The conditions of each run and composition of each mixture is shown in Table 5. Nitrogen diluent provided the balance to the reactor. The results of isopentane conversion as a function of time are shown in FIG. 5. Symbols in FIG. 5 are provided in Table 5.

TABLE 5

| Run | Sample load, g | Temp. ° C. | Hydrocarbon, mol % | Water, mol % | Hydrogen, mol % | Nitrogen, mol % | Hydrocarbon WHSV, hr$^{-1}$ | Res time, s | Symbol in FIG. 5 |
|---|---|---|---|---|---|---|---|---|---|
| A | 1.25 | 650 | 19.8 | 49.5 | — | 30.7 | 1.55 | 0.74 | ◊ |
| B | 0.7 | 650 | 11.0 | 49.4 | — | 39.6 | 1.55 | 0.41 | - |
| C | 0.7 | 650 | 19.8 | 49.5 | — | 30.7 | 2.77 | 0.41 | ● |
| D | 1.25 | 650 | 11.0 | 49.4 | — | 39.6 | 0.87 | 0.74 | □ |
| E | 1.25 | 600 | 19.8 | 49.5 | — | 30.7 | 1.55 | 0.78 | * |
| F | 1.25 | 650 | 21.2 | 26.2 | — | 52.6 | 1.55 | 0.78 | x |
| G | 1.25 | 650 | 11.0 | — | 89.0 | 0.0 | 0.96 | 0.73 | + |
| H | 1.25 | 650 | 27.0 | — | 73.0 | 0.0 | 0.86 | 1.8 | ◆ |
| I | 1.25 | 650 | 11.0 | — | 29.7 | 59.3 | 0.86 | 0.73 | ○ |

Low conversion and fast deactivation is observed in the presence of steam, but high conversion and no deactivation are observed in the presence of hydrogen.

Example 8

Figure 6:
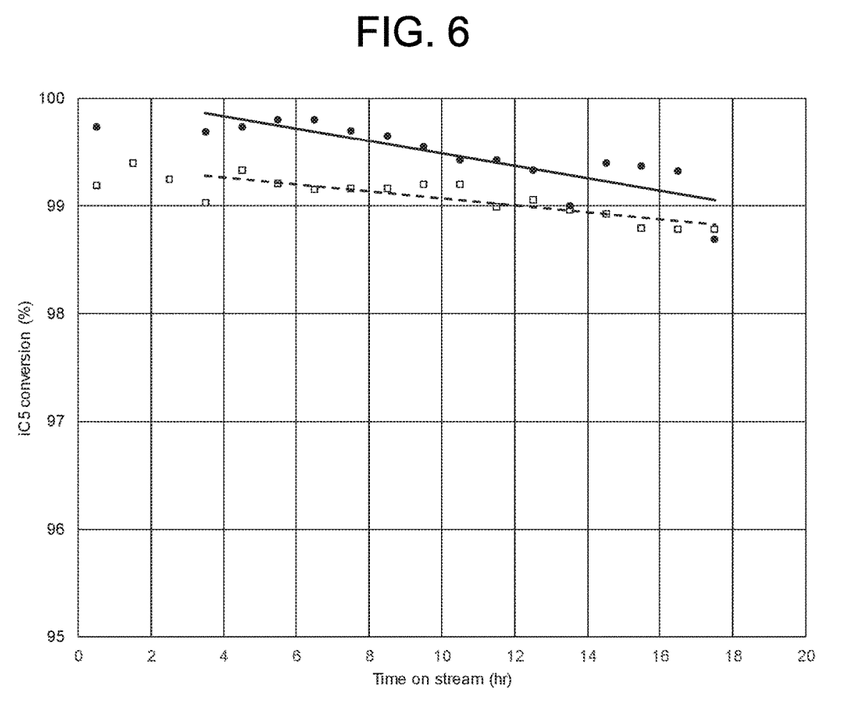
FIG. 6 is a plot of $iC_5$ conversion versus time on stream.

The silicalite catalyst was ground sized to 40×60 mesh. Two grams of the catalyst was loaded in a 9 mm quartz reactor. The reactor was operated at atmospheric pressure and at 600° C. Pure isopentane was fed at 0.0145 mL/min to the reactor after being combined with a gas feed. In two separate runs the gas contained 100 mol % hydrogen or 100 mol % nitrogen, respectively, flowing at 7.5 standard cc/min, such that the molar flow rate of the gas was 2.7 times the molar flow rate of the isopentane. The product mixture was analyzed as vapor by gas chromatography. Isopentane conversion as a function of time on stream is shown in FIG. 6 for the two runs.

When nitrogen gas was used, isopentane conversion deactivated at 1.38% per day after 4 hours on stream as shown by the solid circles. When hydrogen gas was used, isopentane conversion deactivated at 0.78% per day after 4 hours on stream as shown by the squares in FIG. 6.

Example 9

A zeolite-water suspension was prepared by addition of 9,978 g of silicalite, weighed on a volatile-free basis, to 9956 g water while stirring. The zeolite had a molar ratio of silica to alumina of about 420 and was calcined, steamed and acid-washed. The resulting mixture was then circulated through a bead mill for about 10 minutes. Three solutions were prepared: 13,861 g of a solution of aluminum chlorohydrate was weighed out comprising 11.08 wt-% aluminum and 12.64 wt-% chlorine. A solution was prepared containing 44.5 wt-% of hexamethylenetetramine (HMT) in water and a third containing 85.7 wt-% $H_3PO_4$ acid. All solutions were then cooled to about 3 to about 10° C. The silicalite-water suspension and the aluminum chlorohydrate solution were combined by pumping together at 98.2 and 60.9 g/min respectively. The HMT and $H_3PO_4$ solutions were combined with the silicalite/water/aluminum chlorohydrate suspension at rates of 34.8 and 30.8 g/min respectively. The mixture was then pumped through a vibrating tube or cylinder with perforations at the outlet end to form droplets which are directed into a vertical column containing paraffin oil heated to about 90 to about 100° C. As the droplets fall though the oil column, spherical gel particles form and were collected at the outlet. The spheres were then drained of oil, transferred into a vertical washing column and washed for about 1 hour at about 69 to about 72° C. in a continuous flow of water containing about 0.005 to 0.5 wt-% $NH_3$, then washed with water at about 49 cm$^3$/min for about 30 min at about 67 to about 71° C. The washed spheres were drained, dried at about 79 to about 121° C. and oven-calcined in air at about 345 to about 625° C. for about 135 minutes. The preparation yielded the final spherical catalyst. The catalyst had a silicalite to binder ratio of 60/40 by weight and apparent bulk density of 0.547 g/cm$^3$.

Example 10

Sixty cubic centimeters (32.8 g) of a catalyst prepared in Example 9 were loaded in a fixed bed reactor in a furnace in three separate catalyst plugs of 15, 15 and 30 cubic centimeters separated by quartz wool and alpha alumina filler. The reactor was configured such that the reformate feed with the composition shown in Table 6 and specific gravity of 0.82 g/cm$^3$ was vaporized and mixed with hydrogen in a reactor pre-heat zone. Liquid and vapor products were separated at the reactor outlet which was maintained at 172 kPa (gauge) (25 psig). The reactor was heated to 424° C., measured at 2 inches above catalyst bed inlet, under hydrogen, and liquid feed flow was initiated at a flow rate to achieve a WHSV of 3 hr$^{-1}$ and a mole ratio of hydrogen to hydrocarbons of 4.5:1. Then temperature was increased to 496° C. for 10 hours. Finally, temperature was increased to 579° C., liquid feed rate was decreased to achieve a WHSV of 0.9 hr$^{-1}$ and hydrogen flow rate was decreased to achieve mole ratio of hydrogen to hydrocarbons of 3:1 thus comprising a hydrogen concentration of 75 mol %. Flows continued for an additional 40 hours. The gas and liquid products were analyzed separately by gas chromatography. Effluent composition is shown in Table 6.

TABLE 6

Reformate Feed

| Component | Feed, wt % | Product, wt % |
|---|---|---|
| $C_1$ Paraffin | 0.000 | 1.362 |
| $C_2$ Paraffins | 0.000 | 2.198 |
| $C_3$ Paraffins | 0.001 | 2.341 |
| $C_4$ Paraffins | 0.002 | 1.041 |
| $C_5$ Paraffins | 1.829 | 0.998 |
| $C_6$ Paraffins | 11.377 | 3.267 |
| $C_7$ Paraffins | 9.992 | 1.961 |
| $C_8$ Paraffins | 2.742 | 0.485 |
| $C_5$ Naphthenes | 0.022 | 0.000 |
| $C_6$ Naphthenes | 0.316 | 0.065 |
| $C_7$ Naphthenes | 0.431 | 0.295 |
| $C_8$ Naphthenes | 0.305 | 0.107 |
| $C_{5+}$ Aliphatics | 28.1 | 8.6 |
| $C_{9+}$ Paraffins, Naphthenes and Olefins | 0.309 | 0.749 |
| Ethylene | — | 4.189 |
| Propylene | 0.001 | 6.303 |
| $C_4$ Olefins | 0.002 | 2.691 |
| $C_5$ Olefins | 0.056 | 0.486 |
| $C_6$ Olefins | 0.335 | 0.144 |
| $C_7$ Olefins | 0.205 | 0.006 |
| $C_8$ Olefins | 0.141 | 0.044 |
| Benzene | 6.643 | 9.802 |
| Toluene | 18.806 | 23.812 |
| Xylene | 20.940 | 20.870 |
| Ethylbenzene | 3.117 | 0.712 |
| Trimethylbenzene | 8.941 | 8.703 |
| Methyl-Ethyl-Benzene | 6.191 | 1.829 |
| Propyl-Benzene | 1.577 | 0.219 |
| Tetra-Methyl Benzene | 1.810 | 1.491 |
| Di-Methyl-Ethyl Benzene | 0.212 | 9.802 |
| Methyl-Propyl-Benzene | 1.198 | 23.812 |
| Di-Ethyl-Benzene | 0.841 | 20.870 |
| Butyl-Benzene | 0.149 | 0.712 |
| $C_{11+}$ Aromatics | 1.508 | 8.703 |
| Aromatic Alkyls$^a$ | 18.7 | 16.2 |
| Aromatic $C_2$-$C_4$ Alkyls$^a$ | 3.6 | 1.1 |

Yields and conversions are shown in Table 7. Yields, ratios, conversions, and balances were calculated as explained for Example 5.

TABLE 7

| Conversion | |
|---|---|
| $C_{5+}$ Aliphatics | 69.3 |
| Aromatic Methyl | 0 |
| Aromatic Ethyl | 65.3 |
| Aromatic Propyl | 83.6 |
| Aromatic Butyl | 91.9 |
| $C_1$-$C_4$ Aromatic Alkyls | 13 |
| $C_2$-$C_4$ Aromatic Alkyls | 70 |
| $C_{5+}$ Aliphatic and $C_1$-$C_4$- Aromatic Alkyls | 47.0 |

TABLE 7-continued

| Yields | |
|---|---|
| Methane | 2.9 |
| Ethane | 4.7 |
| Ethylene | 9.0 |
| Propane | 5.0 |
| Propylene | 13.5 |
| Butanes | 2.2 |
| Butylenes | 5.7 |
| $C_6$-$C_{10}$ rings | 2.0 |
| $C_{11}+$ | 1.9 |
| $C_1$-$C_4$ olefin | 28.2 |
| $C_1$-$C_4$ paraffin | 14.8 |
| Ratios and Ring Balance | |
| $C_4$-olefin/paraffin ratio | 1.9 |
| $C_6$-$C_{10}$ aromatic ring balance | 101.8 |

Results indicate $C_{5-}$ aliphatics cracked and $C_{4-}$ alkyl aromatics were dealkylated at significant conversion levels to substantial yields of light olefins ethylene, propylene and butylene. Conversion to light olefins is more significant than conversion to light paraffins. Additionally, the $C_6$-$C_{10}$ aromatic ring balance of over 100% indicates that aromatics are being generated in addition to aromatics resulting from dealkylation.

Specific Embodiments

While the following is described in conjunction with specific embodiments, it will be understood that this description is intended to illustrate and not limit the scope of the preceding description and the appended claims.

A first embodiment of the invention is a process for making aromatics comprising taking a cracking feed stream boiling in the naphtha range comprising aromatic compounds and aliphatic compounds, wherein at least a portion of the aromatic compounds contain alkyl groups; passing the cracking feed stream at a temperature of at least 500° C. to a cracking reactor comprising a cracking catalyst including a zeolite with a maximum pore diameter of greater than 5 Angstroms; adding at least about 60 mol % hydrogen to the cracking reactor to preserve the cracking catalyst against deactivation; selectively cracking the aliphatic compounds and selectively dealkylating the alkyl groups on the aromatic compounds in the presence of the cracking catalyst in the cracking reactor under cracking conditions to cracked olefins and aromatic compounds in a cracked effluent stream. An embodiment of the invention is one, any or all of prior embodiments in this paragraph up through the first embodiment in this paragraph further comprising reforming a naphtha stream in a reforming unit under reforming conditions to produce a reformer effluent stream and taking the cracking feed stream from the reformer effluent stream. An embodiment of the invention is one, any or all of prior embodiments in this paragraph up through the first embodiment in this paragraph wherein the zeolite comprises MFI zeolite. An embodiment of the invention is one, any or all of prior embodiments in this paragraph up through the first embodiment in this paragraph wherein the zeolite comprises a silicalite catalyst having a zeolite silica to alumina molar ratio of greater than about 250. An embodiment of the invention is one, any or all of prior embodiments in this paragraph up through the first embodiment in this paragraph wherein the hydrogen mol % in the cracking reactor is no more than 90. An embodiment of the invention is one, any or all of prior embodiments in this paragraph up through the first embodiment in this paragraph wherein the hydrogen partial pressure in the cracking reactor is between about 62 kPa (9 psia) and about 345 kPa (50 psia). An embodiment of the invention is one, any or all of prior embodiments in this paragraph up through the first embodiment in this paragraph wherein the hydrogen to hydrocarbon mole ratio at an inlet to the cracking reactor is at least 2:1. An embodiment of the invention is one, any or all of prior embodiments in this paragraph up through the first embodiment in this paragraph wherein the ratio of olefins to paraffins of $C_{4-}$ hydrocarbons is at least 1 in the cracked effluent stream. An embodiment of the invention is one, any or all of prior embodiments in this paragraph up through the first embodiment in this paragraph wherein the naphtha feed stream has a T5 boiling point in a range of about 0° C. to about 82° C. and a T95 boiling point in a range of about 20° C. to about 215° C. An embodiment of the invention is one, any or all of prior embodiments in this paragraph up through the first embodiment in this paragraph further comprising introducing a naphtha feed stream into a naphtha splitter column to produce at least two streams, the first stream having a T5 boiling point in a range of about 0° C. to about 34° C. and a T95 boiling point in a range of about 25° C. to about 82° C. and the second stream having a T5 boiling point in a range of about 20° C. to about 82° C. and a T95 boiling point in a range of about 140° C. to about 215° C.; passing the second stream to a naphtha hydrotreating reactor to produce a hydrotreated naphtha stream; and wherein reforming the naphtha stream comprises reforming the hydrotreated naphtha stream.

A second embodiment of the invention is a process for making aromatics and light olefins comprising reforming a naphtha stream in a reforming unit under reforming conditions to produce a reformer effluent stream comprising aromatic compounds and aliphatic compounds, wherein at least a portion of the aromatic compounds contain alkyl groups; taking a cracking feed stream from the reformer effluent stream; heating the cracking feed stream to at least 500° C. and passing the cracking feed stream at a temperature of at least 500° C. to a cracking reactor comprising a catalyst including a zeolite having pore size greater than 5 Angstroms; providing at least about 50 mol % hydrogen to the cracking reactor to preserve the cracking catalyst against deactivation while maintaining the hydrogen partial pressure in the cracking reactor is between about 62 kPa (9 psia) and about 345 kPa (50 psia); and selectively cracking the aliphatic compounds and selectively dealkylating the alkyl groups on the aromatic compounds in the presence of the cracking catalyst in the cracking reactor under cracking conditions to cracked and dealkylated olefins and the aromatic compounds in a cracked reformer effluent stream, wherein the cracked olefins comprise at least one of ethylene, propylene, and butylene. An embodiment of the invention is one, any or all of prior embodiments in this paragraph up through the second embodiment in this paragraph wherein the hydrogen mol % in the cracking reactor is no more than 90. An embodiment of the invention is one, any or all of prior embodiments in this paragraph up through the second embodiment in this paragraph further comprising separating the cracked reformer effluent stream into an aromatic lean fraction comprising the cracked olefins and an aromatic rich fraction comprising the aromatic compounds; and passing the aromatic rich fraction to an aromatics complex. An embodiment of the invention is one, any or all of prior embodiments in this paragraph up through the second embodiment in this paragraph wherein the hydrogen to hydrocarbon mole ratio at an inlet to the cracking reactor inlet is at least 2:1. An embodiment of the invention is one, any or all of prior embodiments in this paragraph up through the second embodiment in this paragraph wherein the cracking conditions include at least one of a temperature in the range of about 500° C. to about 700° C., a pressure in a range of about 30 kPa (g) to about 750 kPa (g), a hydrogen to $C_{5+}$ hydrocarbon mole ratio at an inlet to the cracking reactor of at least about 0.5:1 to about 6:1, and a weight hourly space velocity (WHSV) of about 0.1 $hr^{-1}$ to about 4 $hr^{-1}$. An embodiment of the invention is one, any or all of prior embodiments in this paragraph up through the second embodiment in this paragraph further comprising introducing a naphtha feed stream into a naphtha splitter column to form at least two streams, the first stream having a T5 boiling point in a range of about 0° C. to about 34° C. and a T95 boiling point in a range of about 20° C. to about 82° C. and the second stream having a T5 boiling point in a range of about 20° C. to about 82° C. and a T95 boiling point in a range of about 140° C. to about 215° C.; passing the second stream to a naphtha hydrotreating reactor producing a hydrotreated naphtha stream; and wherein reforming the naphtha stream comprises reforming the hydrotreated naphtha stream. An embodiment of the invention is one, any or all of prior embodiments in this paragraph up through the second embodiment in this paragraph further comprising introducing a naphtha feed stream into a naphtha hydrotreating reactor to produce a hydrotreated naphtha stream; passing the hydrotreated naphtha stream to a naphtha splitter column to produce at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.; and wherein reforming the naphtha stream comprises reforming the second hydrotreated stream.

A third embodiment of the invention is a process for making aromatics comprising taking a cracking feed stream boiling in the naphtha range comprising aromatic compounds and aliphatic compounds, wherein at least a portion of the aromatic compounds contain alkyl groups; heating the cracking feed stream to at least 500° C. and passing the cracking feed stream at a temperature of least 500° C. to a cracking reactor comprising a cracking catalyst including a zeolite with having a pore size greater than 5 Angstroms; providing at least about 60 mol % to about 90 mol % hydrogen to the cracking reactor to preserve the cracking catalyst against deactivation; selectively cracking the aliphatic compounds and selectively dealkylating the alkyl groups on the aromatic compounds in the presence of the cracking catalyst in the cracking reactor under cracking conditions to cracked olefins and aromatic compounds in a cracked effluent stream. An embodiment of the invention is one, any or all of prior embodiments in this paragraph up through the third embodiment in this paragraph wherein the hydrogen partial pressure in the cracking reactor is between about 62 kPa (9 psia) and about 345 kPa (50 psia). An embodiment of the invention is one, any or all of prior embodiments in this paragraph up through the third embodiment in this paragraph wherein the hydrogen to hydrocarbon mole ratio at an inlet to the cracking reactor is at least 2:1.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for making aromatics comprising:
providing a cracking feed stream boiling in the naphtha range comprising aromatic compounds and aliphatic compounds, wherein at least a portion of the aromatic compounds contain alkyl groups;
passing the cracking feed stream at a temperature of at least 500° C. to a cracking reactor comprising a cracking catalyst including a zeolite with a maximum pore diameter of greater than 5 Angstroms at a pressure of no more than about 345 kPa (absolute);
adding at least about 60 mol % hydrogen to the cracking reactor to preserve the cracking catalyst against deactivation; and
selectively cracking the aliphatic compounds and selectively dealkylating the alkyl groups on the aromatic compounds in the presence of the cracking catalyst in the cracking reactor under cracking conditions to cracked olefins and aromatic compounds in a cracked effluent stream.

2. The process of claim 1 further comprising reforming a naphtha stream in a reforming unit under reforming conditions to produce a reformer effluent stream and taking said cracking feed stream from said reformer effluent stream.

3. The process of claim 1 wherein the zeolite comprises WI zeolite.

4. The process of claim 1 wherein the zeolite comprises a silicalite zeolite catalyst having a zeolite silica to alumina molar ratio of greater than about 250.

5. The process of claim 1 wherein the hydrogen mol % in the cracking reactor is no more than 90.

6. The process of claim 1 wherein the hydrogen partial pressure in the cracking reactor is between about 62 kPa (9 psia) and about 345 kPa (50 psia).

7. The process of claim 1 wherein the hydrogen to hydrocarbon mole ratio is at least 2:1 at an inlet to the cracking reactor.

8. The process of claim 1 wherein a weight ratio of olefins to paraffins of $C_{4-}$ hydrocarbons is at least 1 in the cracked effluent stream.

9. The process of claim 1 wherein the naphtha feed stream has a T5 boiling point in a range of about 0° C. to about 82° C. and a T95 boiling point in a range of about 20° C. to about 215° C.

10. The process of claim 1 further comprising:
introducing a naphtha feed stream into a naphtha splitter column to produce at least two streams, the first stream having a T5 boiling point in a range of about 0° C. to about 34° C. and a T95 boiling point in a range of about 25° C. to about 82° C. and the second stream having a T5 boiling point in a range of about 20° C. to about 82° C. and a T95 boiling point in a range of about 140° C. to about 215° C.;
passing the second stream to a naphtha hydrotreating reactor to produce a hydrotreated naphtha stream; and
wherein reforming the naphtha stream comprises reforming the hydrotreated naphtha stream.

11. A process for making aromatics and light olefins comprising:
reforming a naphtha stream in a reforming unit under reforming conditions to produce a reformer effluent stream comprising aromatic compounds and aliphatic compounds, wherein at least a portion of the aromatic compounds contain alkyl groups;
taking a cracking feed stream from the reformer effluent stream;
heating the cracking feed stream to at least 500° C. and passing the cracking feed stream at a temperature of at least 500° C. to a cracking reactor comprising a catalyst including a zeolite having pore size greater than 5 Angstroms and a zeolite silica to alumina molar ratio of greater than about 250;
providing at least about 50 mol % hydrogen to the cracking reactor to preserve the cracking catalyst against deactivation while maintaining the hydrogen partial pressure in the cracking reactor is between about 62 kPa (9 psia) and about 345 kPa (50 psia); and
selectively cracking the aliphatic compounds and selectively dealkylating the alkyl groups on the aromatic compounds in the presence of the cracking catalyst in the cracking reactor under cracking conditions to cracked and dealkylated olefins and the aromatic compounds in a cracked reformer effluent stream, wherein the cracked olefins comprise at least one of ethylene, propylene, and butylene.

12. The process of claim 11 wherein the hydrogen mol % in the cracking reactor is no more than 90.

13. The process of claim 11 further comprising separating the cracked reformer effluent stream into an aromatic lean fraction comprising the cracked olefins and an aromatic rich fraction comprising the aromatic compounds; and passing the aromatic rich fraction to an aromatics complex.

14. The process of claim 11 wherein the hydrogen to hydrocarbon mole ratio in the cracking reactor is at least 2:1.

15. The process of claim 11 wherein the cracking conditions include at least one of a temperature in the range of about 500° C. to about 700° C., a pressure in a range of about 30 kPa (g) to about 750 kPa (g), a hydrogen to $C_{5+}$ hydrocarbon mole ratio at an inlet to the cracking reactor of at least about 1:1 to about 6:1, and a weight hourly space velocity (WHSV) of about 0.1 $hr^{-1}$ to about 4 $hr^{-1}$.

16. The process of claim 14 further comprising:
introducing a naphtha feed stream into a naphtha splitter column to form at least two streams, the first stream having a T5 boiling point in a range of about 0° C. to about 34° C. and a T95 boiling point in a range of about 20° C. to about 82° C. and the second stream having a T5 boiling point in a range of about 20° C. to about 82° C. and a T95 boiling point in a range of about 140° C. to about 215° C.;
passing the second stream to a naphtha hydrotreating reactor producing a hydrotreated naphtha stream; and
wherein reforming the naphtha stream comprises reforming the hydrotreated naphtha stream.

17. The process of claim 14 further comprising:
introducing a naphtha feed stream into a naphtha hydrotreating reactor to produce a hydrotreated naphtha stream; and
passing the hydrotreated naphtha stream to a naphtha splitter column to produce at least two streams, the first hydrotreated stream having a T5 boiling point in a range of about 0° C. to about 34° C. and a T95 boiling point in a range of about 25° C. to about 82° C. and the second hydrotreated stream having a T5 boiling point in a range of about 20° C. to about 82° C. and a T95 boiling point in a range of about 140° C. to about 215° C.;

wherein reforming the naphtha stream comprises reforming the second hydrotreated stream.

18. A process for making aromatics comprising:

taking a cracking feed stream boiling in the naphtha range comprising aromatic compounds and aliphatic compounds, wherein at least a portion of the aromatic compounds contain alkyl groups;

heating the cracking feed stream to at least 500° C. and passing the cracking feed stream at a temperature of least 500° C. to a cracking reactor comprising a cracking catalyst including a zeolite with having a pore size greater than 5 Angstroms and a zeolite silica to alumina molar ratio of greater than about 250;

providing at least about 60 mol % to about 90 mol % hydrogen to the cracking reactor to preserve the cracking catalyst against deactivation;

selectively cracking the aliphatic compounds and selectively dealkylating the alkyl groups on the aromatic compounds in the presence of the cracking catalyst in the cracking reactor under cracking conditions to cracked olefins and aromatic compounds in a cracked effluent stream wherein a weight ratio of olefins to paraffins of $C_{4-}$ hydrocarbons is at least 1 in the cracked effluent stream.

19. The process of claim 18 wherein the hydrogen partial pressure in the cracking reactor is between about 62 kPa (9 psia) and about 345 kPa (50 psia).

20. The process of claim 19 wherein the hydrogen to hydrocarbon mole ratio is at least 2:1 at an inlet to the cracking reactor.

\* \* \* \* \*